US006689112B1

(12) United States Patent
Blanchard et al.

(10) Patent No.: US 6,689,112 B1
(45) Date of Patent: Feb. 10, 2004

(54) SANITARY NAPKIN HAVING CONFORMABLE SIDE FLAPS

(75) Inventors: Stephen John Blanchard, North Brunswick, NJ (US); Catherine E. Salerno, Millington, NJ (US); James P. Barr, East Amwell, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 109 days.

(21) Appl. No.: 09/723,856

(22) Filed: Nov. 28, 2000

(51) Int. Cl.[7] ............................................... A61F 13/15
(52) U.S. Cl. ................................................. 604/385.04
(58) Field of Search ........................ 604/385.01–385.05, 604/385.21, 385.22

(56) References Cited

U.S. PATENT DOCUMENTS

| 4,917,697 A | 4/1990 | Osborn, III et al. |
|---|---|---|
| 4,940,462 A | 7/1990 | Salerno |
| 5,009,653 A | 4/1991 | Osborn, III |
| 5,650,223 A * | 7/1997 | Weinberger et al. .......... 442/62 |
| 5,704,930 A | 1/1998 | Lavash et al. |
| 6,077,255 A * | 6/2000 | Hunter et al. ............... 604/387 |
| 6,280,428 B1 * | 8/2001 | Lash et al. ............. 604/385.04 |

* cited by examiner

Primary Examiner—Weilun Lo
Assistant Examiner—C. Lynne Anderson
(74) Attorney, Agent, or Firm—James P. Barr (57) ABSTRACT

Absorbent articles having a central absorbent element that is adapted to be worn in a crotch portion of a wearer's undergarment are provided with a pair of flaps, one flap extending laterally from each respective longitudinal side of the central absorbent element. The flaps are flexible and adapted to be folded over the edges of a wearer's undergarment. A central portion of the flap is formed from a flexible, elastic material having an elastic modulus and an adjacent corner region of the flap is formed from a substantially non-extensible, non-elastic flexible material.

3 Claims, 8 Drawing Sheets

SANITARY NAPKIN HAVING CONFORMABLE SIDE FLAPS

FIELD OF THE INVENTION

The present invention relates to absorbent articles such as sanitary napkins, adult incontinence devices, and the like. The absorbent articles have a central absorbent element that is adapted to be worn in a crotch portion of a wearer's undergarment and are provided with a pair of flaps, one flap extending laterally from each respective longitudinal side of the central absorbent element. The flaps are flexible and adapted to be folded over the edges of a wearer's undergarment. A central portion of the flap is formed from a substantially non-extensible flexible material and adjacent corner portions of the flap are formed from flexible, elastic materials having an elastic modulus.

BACKGROUND OF THE INVENTION

Numerous types of absorbent articles for the absorption of body fluids such as menses, urine, and feces are well known in the art. Absorbent articles, particularly sanitary napkins, having flexible side flaps (which are also commonly referred to as wings or tabs) are disclosed in the literature and are commercially available.

In general, the flaps extend laterally from a central absorbent element and are adapted to be folded around the edges of the wearer's undergarment in the crotch region when in use. Thus, in use the flaps are disposed between the edges of the wearer's undergarment in the crotch region and the wearer's thighs. Commonly, the flaps are provided with an attachment means for affixing the flaps to the underside of the wearer's undergarment. The flaps serve to prevent exudates from soiling the edges of the wearer's undergarment and to help stabilize the napkin from shifting out of place.

Sanitary napkins having flaps of the various types are well known in the art. While sanitary napkins having flaps are commonly viewed as providing better protection against soiling as compared to sanitary napkins without flaps, the napkins having flaps commonly experience problems that keep them from being optimally effective. These problems generally result from the stresses exerted on the flaps from a wearer's undergarment when the sanitary napkins are worn.

More particularly, when the flaps are folded over the edges of the wearer's undergarment, stresses are imparted by the user's undergarment to the corner regions of the flaps. That is, the stresses are especially high along the fold line at the edges of the wearer's undergarment where the flaps are folded from the body-side of the undergarment to the underside of the undergarment due to an inability of a linearly folded flap to accommodate the curved configuration of the crotch portion of the undergarment. These stresses are magnified when a wearer sits or crouches because the edges of the undergarment are pulled outward against the flaps thus increasing the forces against this fold line. When the stresses become too high, the flaps may become detached from the undergarment and some portion of the aforementioned benefits of the flaps may be lost. In addition, even if the stresses are not sufficient to detach the flaps, they may still be sufficient to cause the flaps to bunch longitudinally creating creases in a proximal portion of the flap. This effectively reduces the length of the flaps and thus reduces the area of coverage of the wearer's undergarments. The stresses described above can also unduly limit the size of the flaps used with an absorbent article since the stresses are typically greater in products having large flaps (that is flaps having a relatively large longitudinal dimension). Thus, there is a need for a way of eliminating or substantially reducing the stresses that develop in the flaps in use, so as to prevent them from becoming detached from the wearer's undergarment and losing ability to cover a given area of the undergarment.

A number of variations on the types of flaps described above have been presented in an attempt to solve various problems. For example, sanitary napkins have been provided with flaps affixed inward from the longitudinal edge of the napkin, sanitary napkins have been provided with elastic means for providing greater convex shape to the body-facing portion of the central absorbent and for enabling adhesive-free placement of the flaps of the napkin. Sanitary napkins have been provided with longitudinally expandable flaps and sanitary napkins have been provided with laterally extensible zones in the flaps. While these approaches serve to help relieve the stresses that occur when flaps fold along a curved undergarment crotch, the invention requires the formation of excess material along the second portion of the flap. Since this material is devoid of elastic memory, the excess is present whether it is required by the particular shape of the undergarment or not, thus presenting the possibility of discomfort to the wearer owing to bunching of the excess material. Thus there is a need to correct the weaknesses of the prior known designs such as described above.

SUMMARY OF THE INVENTION

It is an object of this invention to provide an absorbent article having side flaps that are adapted to be folded over a crotch portion of an undergarment, the flaps being adapted to relieve stresses that may develop in the corner regions of the flap.

In accordance with the present invention, there has been provided a sanitary napkin comprising a central absorbent element having a cover layer, a barrier layer and an absorbent core between the cover layer and the barrier layer, the central absorbent element having opposite longitudinally extending edges and opposite lateral ends, a flap extending laterally from each respective longitudinal edge along a line of juncture and adapted to be folded over a crotch portion of an undergarment in use, each flap having a central region and a corner region adjacent the line of juncture and a lateral centerline extending through the central region and bisecting the flap into first half and a second half;

the central region of the flap adjacent the flap lateral centerline being formed from a layer of a non-tensioned flexible, elastic film material having an elastic modulus and at least a portion of each corner region being formed from a substantially non-elastic material wherein the central region is capable of elastically expanding in use to permit each corner region to smoothly conform to the crotch portion of the undergarment.

DETAILED DESCRIPTION OF PREFERRED EMBODIMENTS

The present invention is directed to an absorbent article that is adapted to be worn in an undergarment for the purpose of absorbing and containing body exudates. The absorbent articles include sanitary napkins, panty liners, incontinent pads, as well as other similar articles worn in the crotch region of a garment. More particularly, the present invention relates to an absorbent article having flexible side flaps that are adapted to be folded over the edges of a crotch portion of a wearer's undergarments and attached to the underside of the undergarments in use. The flaps are provided with zones of extensibility for relieving the stresses that develop in the flaps in use. More particularly, it has been found that by forming the central region of the flap from a layer of an non-tensioned elastic material such that the central region is extensible in use, that the flap is able elastically deform to enable each corner region to maintain a close and smooth fit around the undergarment.

The ability of a flap to maintain a close and smooth fit has been found to provide better comfort to the wearer and more complete flap protection to the undergarment. The elastic materials must have an elastic modulus that is capable of imparting elastic memory to the extensible portion of the flap. As used herein the terminology "elastic modulus" refers to the ability of a material to expand and to recover its substantially original size with the application and release of an applied external force to that material. The inclusion of elastic modulus to a central portion of the flap allows the flap to expand to the extent necessary and permits that portion of the flap to retract when force is no longer applied. This eliminates the potential for bunching or wrinkling of excess material. Moreover, the present invention provides greater design flexibility by allowing the corner regions of the flap to be formed from a continuous extension of either the topsheet, the back sheet or a combination of both the topsheet and backsheet material. The non-expandable corner regions of the flap preferably have an attachment means on a garment faceable surface thereof.

Referring to FIGS. 1 and 2a–c, there is shown a preferred embodiment of an absorbent article of the present invention wherein the absorbent article is a sanitary napkin 10. The sanitary napkin 10 has a principal longitudinal centerline and a principal lateral centerline. The term "longitudinal", as used herein, refers to a line, axis or direction which lies within the plane of the sanitary napkin that is generally parallel to a vertical plane which bisects a standing wearer into left and right body halves when the sanitary napkin is worn. The term "lateral", as used herein refers to a line, axis, or direction which lies within the plane of the sanitary napkin that is generally perpendicular to the longitudinal direction. The sanitary napkin 10 has a central absorbent element 20 that is adapted to be worn in a crotch portion of a user's undergarment. The central absorbent element 20 of the sanitary napkin 10 comprises a body faceable liquid pervious topsheet 15, a garment faceable liquid impervious backsheet 17. Positioned between the topsheet and the backsheet is an absorbent core 19. The central absorbent element 20 has opposite longitudinal edges 25, 25'.

Figure 10:
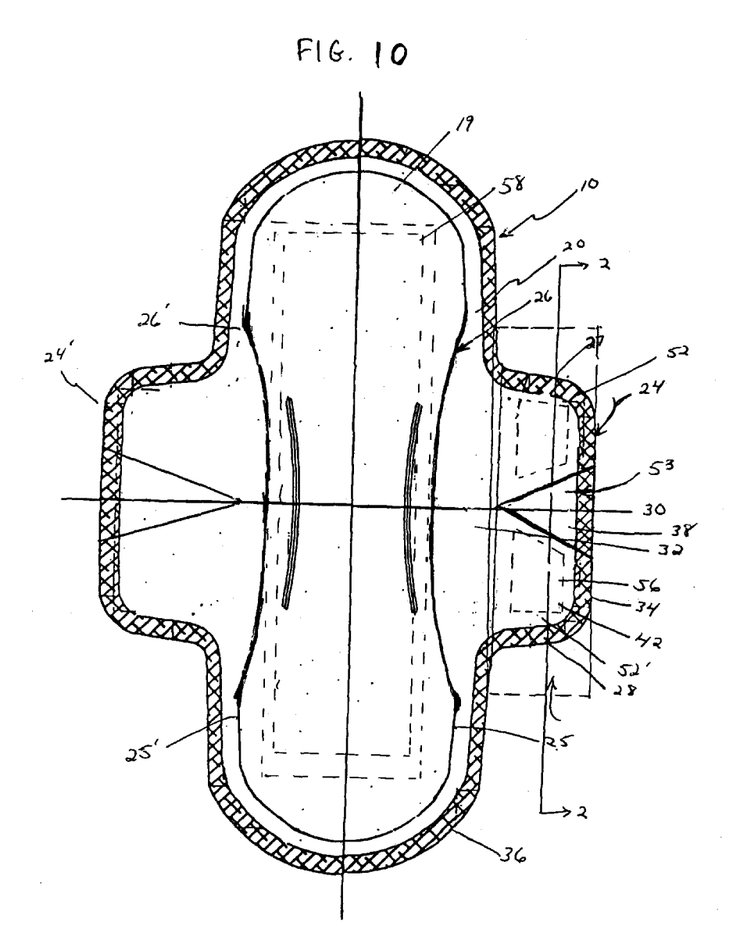
FIG. 10 is a top plan view of another embodiment of the present invention.

The sanitary napkin 10 further includes a pair of flexible side flaps 24, 24', each side flap extending laterally outward from a respective longitudinal side edge 25, 25' of the central absorbent element 20 along a respective line of juncture 26, 26'. The line of juncture is typically a longitudinally oriented region where the flaps 24 extend from or are joined to the central absorbent element 20. The line of juncture may be any of various curved or straight lines and may comprise a continuous line or may comprise a plurality intermittent lines or points of attachment. In the embodiment illustrated in FIG. 10, the line of juncture 26 is a longitudinally oriented curved line. In the embodiment illustrated in FIG. 1, the line of juncture 26 is a relatively straight continuous line. The flaps may be affixed to and extend directly outwardly from the line of juncture along the longitudinal side edges of the central absorbent element 20 (as described more fully in U.S. Pat. No. 4,687,478, which is incorporated herein by reference in its entirety). Alternatively, the flaps may be affixed to and extend laterally from a line of juncture on a garment faceable side of the sanitary napkin inward from the longitudinal edges of the central absorbent element 20 (as described more fully in U.S. Pat. No. 4,900,320, which is incorporated herein by reference in its entirety). In either execution, the flap 24 has a central portion 53 and two corner regions 52, 52'.

Figure 1:
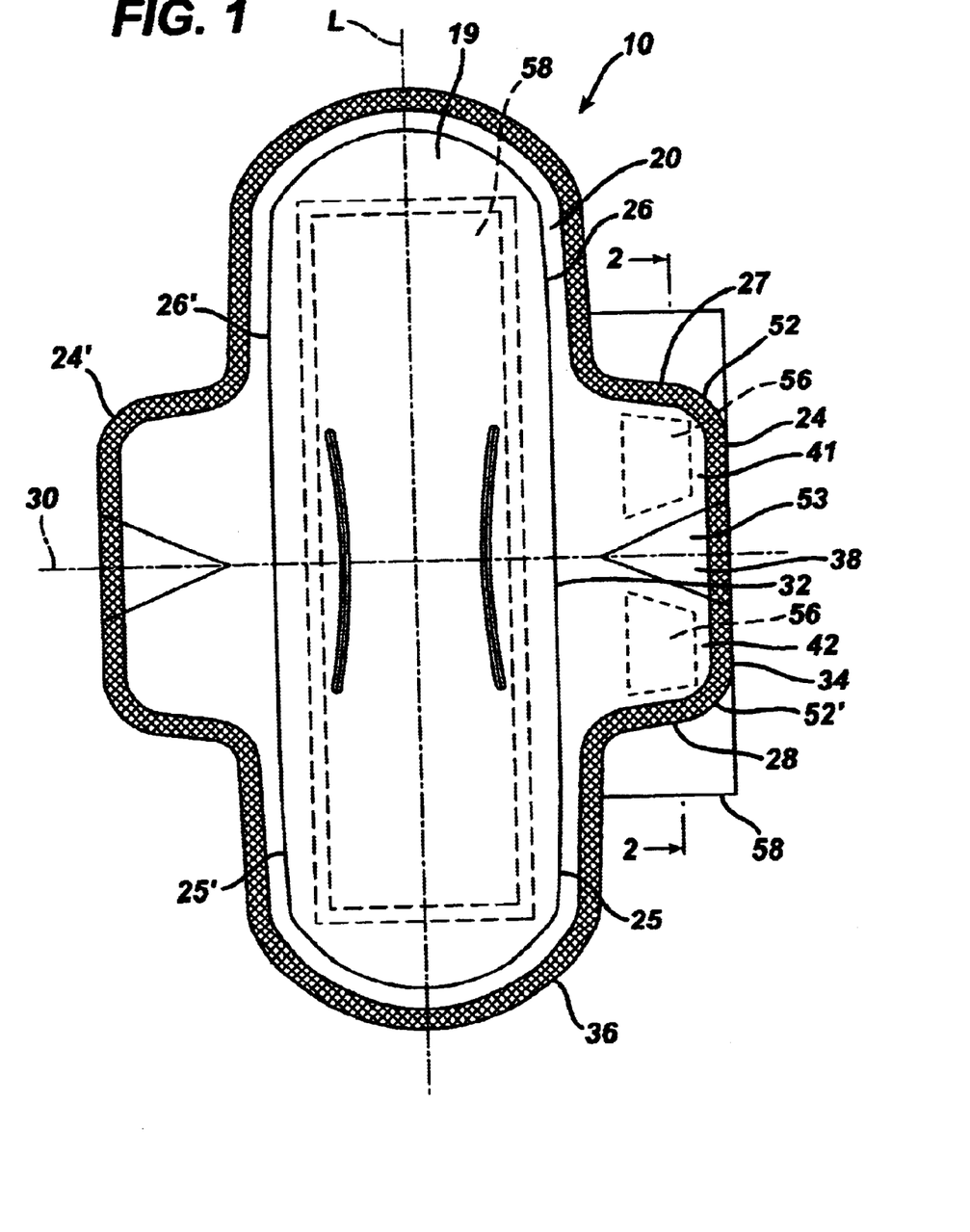
FIG. 1 is a top plan view of a sanitary napkin of the present invention.
Figure 3:
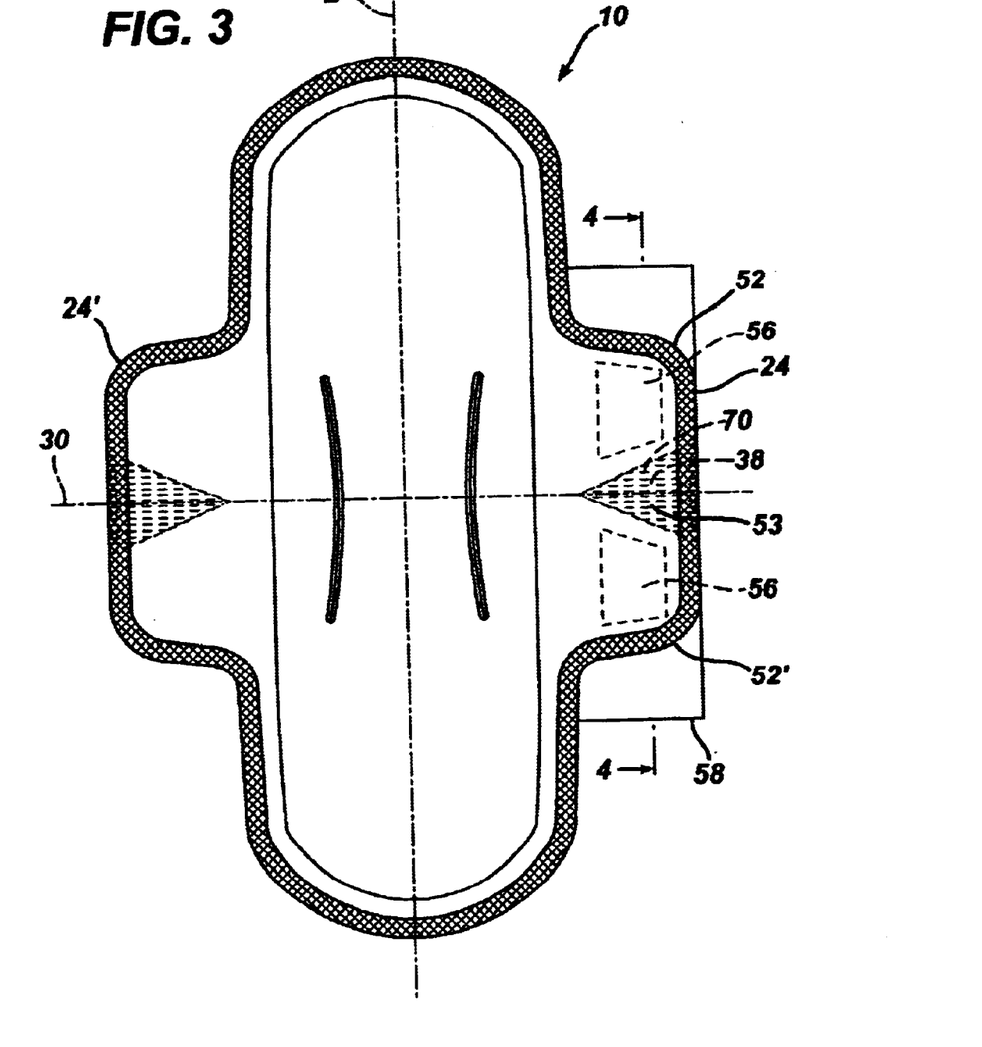
FIG. 3 is a top plan view of an another embodiment of the present invention.

Each flap 24 extends from a proximal edge 32 along the line of juncture and extends laterally outward to a distal edge (or "freely extending end") 34 laterally remote from the line of juncture 26. The flaps are divided into a first half 41 and a second half 42 by an imaginary flap lateral centerline 30 intermediate flap lateral edges 27, 28. The flap lateral centerline 30 bisects a central portion 53 of the flap. The central portion 53 of each flap 24 adjacent the flap lateral centerline, is formed from a layer of flexible, elastic material 38 having an elastic modulus. The flexible elastic material is preferably an elastic formed film, that allows the central portion to elastically expand and retract to a greater degree than the corner regions of the sanitary napkin located remote from the flap lateral centerline. It is preferred that the elastic material has a low modulus of stretch. As used herein, the terminology "low modulus of stretch" refers to the ability of the elastic material to easily and preferentially deform in use when stresses are imparted by a user's undergarment. That is, it is preferred that the edge of the undergarment maintain its substantially original orientation and not be deformed or re-shaped due to the presence of the flap. Thus, the expandable center portion 53 provides a means for the relief of stresses in the flaps of the sanitary napkin when the sanitary napkin is placed in the wearer's undergarment. While it is possible to include non-expandable materials into the central portion 53, it is important that these non-expandable materials be treated to allow the central portion 53 to expand. One example of a suitable treatment means, as shown in FIG. 3, includes slitting the non-expandable flap materials in an amount sufficient to permit the elastomeric materials to expand. The flap lateral centerline 30 will generally coincide with the principal lateral centerline but such is not required. Each flap half has a corner region 52 located adjacent the line of juncture along the proximal edge of the flap. The corner regions are located along the proximal edge of the flap and are preferably spaced apart from the flap lateral centerline in a longitudinal direction. The corner region of each flap is formed from at least one layer of material that is substantially non-elastic under normal conditions of use.

Figure 2A:
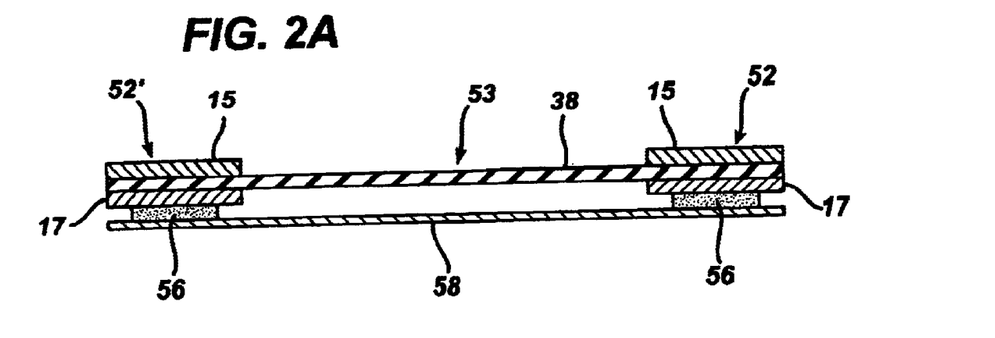
FIG. 2a is a lateral cross section view of a first embodiment of the flap portion taken along line 2—2 of FIG. 1.

Referring to FIGS. 2a–c, there are shown cross sectional views of three embodiments of the flap 24 of FIG. 1. In FIG. 2a, the central portion 53 comprises a single, continuous layer of a flexible, elastic material 38 having an elastic modulus. The corner regions 52, 52' are formed from a continuous extension of the topsheet 15 and backsheet 17. The layer of flexible, elastic material 38 is affixed intermediate the topsheet 15 and the backsheet 17 and is generally coterminous with the lateral ends thereof. The garment-faceable surface of the corner regions of the flap 24 is coated with a flap adhesive 56. A removable release liner 58 covers the flap adhesive 56.

Figure 2B:
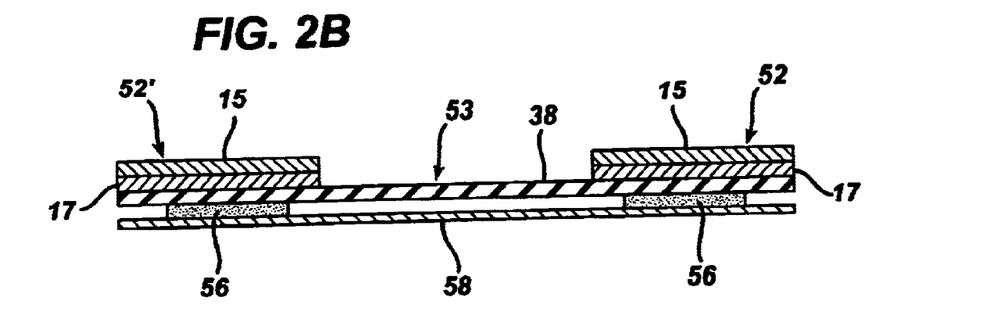
FIG. 2b is a lateral cross section view of a second embodiment of the flap portion taken along line 2—2 of FIG. 1.

In FIG. 2b, the central portion 53 comprises a single, continuous layer of a flexible, elastic material 38 having an elastic modulus. The corner regions 52, 52' are formed from a continuous extension of the topsheet 15 and backsheet 17. The layer of flexible, elastic material 38 is affixed to a garment faceable surface of the backsheet 17 and is generally coterminous with the lateral ends thereof. The garment-faceable surface of flap 24 is coated with a flap adhesive 56. A removable release liner 58 covers the flap adhesive 56.

Figure 2C:
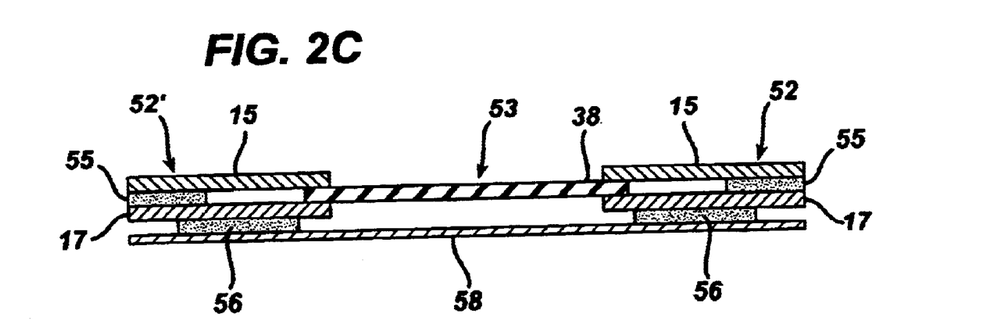
FIG. 2c is a lateral cross section view of a third embodiment of the flap portion taken along line 2—2 of FIG. 1.

In FIG. 2c, the central portion 53 comprises a single, continuous layer of a flexible, elastic material 38 having an elastic modulus. The corner regions 52, 52' are formed from a continuous extension of the topsheet 15 and backsheet 17. The layer of flexible, elastic material 38 is affixed intermediate a portion of the topsheet 15 and the backsheet 17. A laminating adhesive 55 affixes at least a portion of the topsheet 15 to the backsheet 17. The garment-faceable surface of flap 24 is coated with a flap adhesive 56. A removable release liner 58 covers the flap adhesive 56.

Each flap 24 is substantially planar prior to use, wherein the corner regions 52, 52' lie within the same plane as the central portion 53 of the flap. However, in use, the substantially non-elastic central portion 53 expands beyond its original dimensions while the corner regions 52, 52' maintain their original dimensions. This enables the corner regions of the flap to form a complex three-dimensional shape to smoothly contour to the shape of the wearer's undergarment.

FIGS. 1 and 2a–c show a preferred embodiment of the present invention wherein the corner regions 52, 52' of the flap are formed by a continuous extension of the topsheet 15 and/or backsheet 17 wherein at least one of these layers is substantially non-elastic under normal use conditions. It is preferred that the central portion 53 has a greater flexure resistance than the corner regions 52, 52'. The central portion 53 has a substantially triangular shape wherein the sides are substantially continuously divergent from the line of juncture along the proximal edge 32 of the flap towards the distal edge 34 of the flap 24. Alternatively, the central portion 53 may be substantially trapezoidal in shape wherein the base of the trapezoid forms at least a portion of the distal edge 34 of the flap and the top (i.e. the side opposite the base) of the trapezoid forms a portion of the proximal edge 32 of the flap. The layer of elastically expandable material 38 that forms the central portion 53 is affixed to each corner region 52.

The overall size of the flaps 24 can be readily selected by those skilled in the art. Preferably, the flaps 24 are sized so that the sanitary napkin 10 is from about 10 to about 23 centimeters wide between the distal edges 34 of the flaps at their greatest separation. Preferably each flap 24 is from about 5 to at least about 19 centimeters long in the direction parallel to the principal longitudinal centerline 1 of the sanitary napkin.

While the above described flaps are shown as being substantially trapezoidal, the shape of the flaps 24 is not critical to the invention and a suitable shape can be readily selected by those skilled in the art. Preferably, the flaps 24 are mirror images of each other and more preferably the two halves 41 and 42 of each flap are also symmetrical about the flap lateral centerline 30. Each flap 24 is associated with the central absorbent element 20 along line of juncture 26. The line of juncture can be concave, straight, (or, but preferably not convex) relative to the principal longitudinal centerline. The line of juncture 26 generally represents a line of demarcation between the central absorbent element 20 and the flaps 24 (although it is not necessary that there be a precise line of demarcation).

When the flaps of the present invention are wrapped around the side edges of a crotch portion of an undergarment, the central portion is capable of elastically expanding to allow the corner regions to resiliently form a three dimensional complex shape to contour to the shape of the undergarment. It should be understood however, that the precise shape of the corner region 52 or the central portion 53 is not per se critical, provided of course that the location and expansion properties enable the flap to conform to the shape of the undergarment. Likewise it is not critical for there to be precise line of demarcation that marks the boundaries of the corner region 52 (or the boundaries of the complementary central portion 53 of the flap). Thus, there can be a gradual transition between the corner region 52 and the central portion 53 of the flap 24.

The elastically expandable material 38 is preferably impervious to fluid, but may be comprised of a material that is merely fluid resistant. In one preferred embodiment, the elastically expandable material is a laminate comprised of a layer of elastomeric film positioned between 2 layers of a stretchable non-woven fabric. An appropriate elastically expandable material provides a degree of maximum expansion such that when the flaps are folded, the central portion is fully expanded allowing the corner regions of the flap along the fold line to follow the radius of curvature of a typical undergarment. The ability to follow the radius of curvature of the undergarment would be effected by the degree of maximum expansion provided by the elastically expandable material 38. In general, elastically expandable material providing approximately 100% elongation at maximum expansion should provide adequate expandability.

The elastically expandable material used to form the central portion may be attached to the corner regions of the flap by any conventional means, including but not limited to adhesive attachment, or heat or sonic sealing. In accordance with an optional embodiment, a sheet of elastically expandable material may be attached to and entirely cover the central portion of the flap formed by the extensions of the topsheet and/or backsheet that extend along the flap corner regions. Alternatively, the elastically expandable material may located solely in the center portion of the flap. In yet another alternative embodiment, the elastically expandable material may form the entire cover sheet 15 layer or the entire backsheet 17 layer of the sanitary napkin and thus extend over the entire pad including the corner regions and central portions of the flaps.

Figure 4:
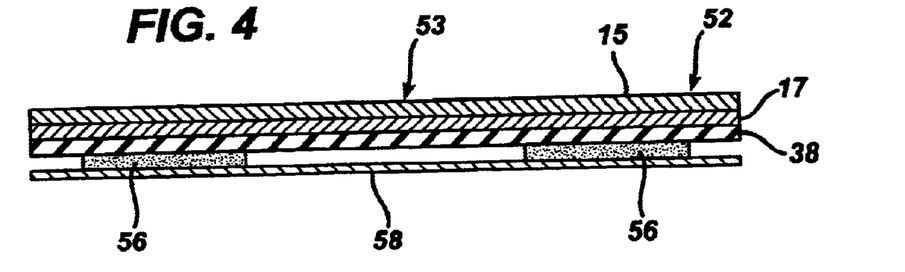
FIG. 4 is a lateral cross section view of a first embodiment of the flap portion along line 4—4 of FIG. 3.

The corner region 52 may be bounded along the proximal edge 32 of the flap 24, which can be located either outward of the absorbent core (as shown in FIGS. 1 and 2), or proximal of the absorbent core (as shown in FIGS. 3 and 4). It is preferred that the corner region be located in the area of the flap which is adapted to be folded over the undergarment. The corner region 52 can extend along the entire proximal edge 32 of the flap 24. Preferably, however, the expandable material 38 is located solely in the central portion 53 of the flap 24.

Sanitary napkin 10 includes topsheet 15, which is formed from a flexible, liquid permeable material, and when the sanitary napkin 10 is in use, the topsheet 15 is in close proximity to the skin of the user. The topsheet 15 is compliant, soft feeling, and non-irritating to the user's skin. It can be made from any of the materials conventional for this type of use. Examples of suitable materials that can be used as topsheet 15 include, but are not limited to woven and nonwoven polyester, polypropylene, nylon, and rayon and formed thermoplastic films.

The absorbent core 19 is positioned between the topsheet 15 and the backsheet 17. The absorbent core 19 provides the means for absorbing menstrual fluid. The absorbent core 19 need not have an absorbent capacity much greater than the total anticipated amount of menstrual fluid to be absorbed. Preferably, the absorbent core 19 has an absorbent capacity of at least 8 grams of fluid. The absorbent core 19 is generally compressible, conformable, and non-irritating to the user's skin. It can comprise any material used in the art for such purpose. Examples include comminuted wood pulp that is generally referred to as airfelt, creped cellulose wadding, absorbent foams, absorbent sponges, synthetic staple fibers, polymeric fibers, hydrogel-forming polymer gelling agents, peat moss, or any equivalent material or combinations of materials.

Polymeric gelling agents are those materials which, upon contact with fluids (i.e., liquids) such as water or body fluids, imbibe such fluids and thereby form hydrogels. In this manner, fluids discharged into the absorbent core 19 can be acquired and held by the polymeric gelling agent, thereby providing the articles herein with enhanced absorbent capacity and/or improved fluid retention performance.

The polymeric gelling agent that is employed in the absorbent core 19 will generally comprise particles of a substantially water-insoluble, slightly cross-linked, partially neutralized, hydrogel-forming polymer material. The term "particles", as used herein, can refer to particles in any form, such as in the form of pellets, flakes, or fibers. The characteristics of the absorbent core 19 (including, but not limited to the preferred types of polymer materials used therein, and types of methods which can be used for preparing these polymer particles) are described in greater detail in U.S. Pat. No. 5,009,653 issued to Osborn and the patents incorporated by reference in that patent, the disclosures of which are all incorporated by reference herein.

In one preferred embodiment, the absorbent core 19 is a laminate comprised of a layer of superabsorbent polymer material (not shown), such as in the form of particles, disposed between two air-laid tissues (not shown), first and second tissue layers (or "upper" and "lower" tissue layers). The first and second tissue layers provide containment of the superabsorbent polymer material, improve lateral wicking of the absorbed exudates throughout the absorbent core 19 and provide a degree of absorbency.

A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, entitled "Composition For Absorbent Film And Method Of Preparation", which issued to Pedersen et al. on Aug. 21, 1984, and U.S. Pat. No. 4,260,443, entitled "Laminated Absorbent Process", which issued to Lindsay et al. on Apr. 7, 1981.

The backsheet 17 is impervious to liquids and, thus, prevents menstrual fluid from soiling the clothing of the user. Any material used in the art for such purpose can be utilized herein. Suitable materials include embossed or non-embossed polyethylene films and laminated tissue. A suitable polyethylene film is manufactured by Monsanto Chemical Corporation and marketed in the trade as Film No. 8020.

As shown in FIG. 1, the topsheet 15 is secured to backsheet 17 along a seam 36 (often referred to as a flange). The seam 36 can be formed by any means commonly used in the art for this purpose such as by gluing, crimping, or heat-sealing. The seam 36 is illustrated in FIG. 1 as extending completely around the periphery of the central absorbent element 20. This is a preferred embodiment for ease of construction. (Other means of uniting the various elements can be used.) The central absorbent element 20 is preferably relatively thin, i.e. having a caliper less than 5 mm.

FIGS. 1 and 2a–d also show adhesive attachment means that are adapted to secure the sanitary napkin 10 to the crotch region of an undergarment. The adhesive attachment means include central pad adhesive 54 and flap adhesive 56. The central pad adhesive 54 provides an adhesive attachment means for securing central absorbent element 20 in the crotch portion of a undergarment. The garment-faceable surface of flap 24, adjacent the distal edge 34 of the flap, is preferably coated with a flap adhesive 56. It is preferred that the flap adhesive 56 be located solely in the non-expandable central portion 53 of the flap 24. The flap adhesive 56 assists in maintaining the flap 24 in position after it is wrapped around the edge of the crotch portion of the undergarment by attaching the flap 24 to the undergarment. Alternatively, the length of the flap may be adapted such that one flap may be attached to the opposing flap. Suitable adhesive fasteners are described in greater detail in U.S. Pat. No. 4,917,697.

The adhesive attachment means are respectively covered by removable release liners, central pad release liner and flap release liner, both designated 58. The pressure-sensitive adhesives should be covered with release liners 58 to keep the adhesives from sticking to extraneous surfaces prior to use. Suitable release liners are described in U.S. Pat. No. 4,917,697 which is incorporated by reference herein.

FIGS. 3 and 4 show a sanitary napkin 10 having another type of expandable flap 24. In this embodiment, the central portion 53 is formed by laminating a layer of an elastically expandable material 38 having an elastic modulus to the topsheet 15 and/or backsheet 17 and providing a plurality of slits 70 through the layers in a manner that will allow elastic expansion. The central portion 53 thus includes a layer of an elastically expandable material 38 as well as the topsheet 15 and/or the backsheet 17. In a preferred embodiment, only the topsheet 15 and/or the backsheet contain slits 70 the elastically expandable material 38 is free of any slits.

Referring to FIG. 4, there is shown a cross sectional view of the flap 24 of FIG. 3. In FIG. 4, the flap 24 comprises a continuous extension of the topsheet 15 and backsheet 17. Affixed to a garment faceable surface of the backsheet 17 is a single, continuous layer of a flexible, elastic material 38 having an elastic modulus. The elastic material 38 is coextensive with the topsheet 15 and backsheet 17. The corner regions 52, 52' are substantially free of any slits whereas central portion 53 has a plurality of slits (not shown) extending through both the topsheet 15 and backsheet 17. The garment-faceable surface of flap 24 is coated with a flap adhesive 56. A removable release liner 58 covers the flap adhesive 56.

Figure 5:
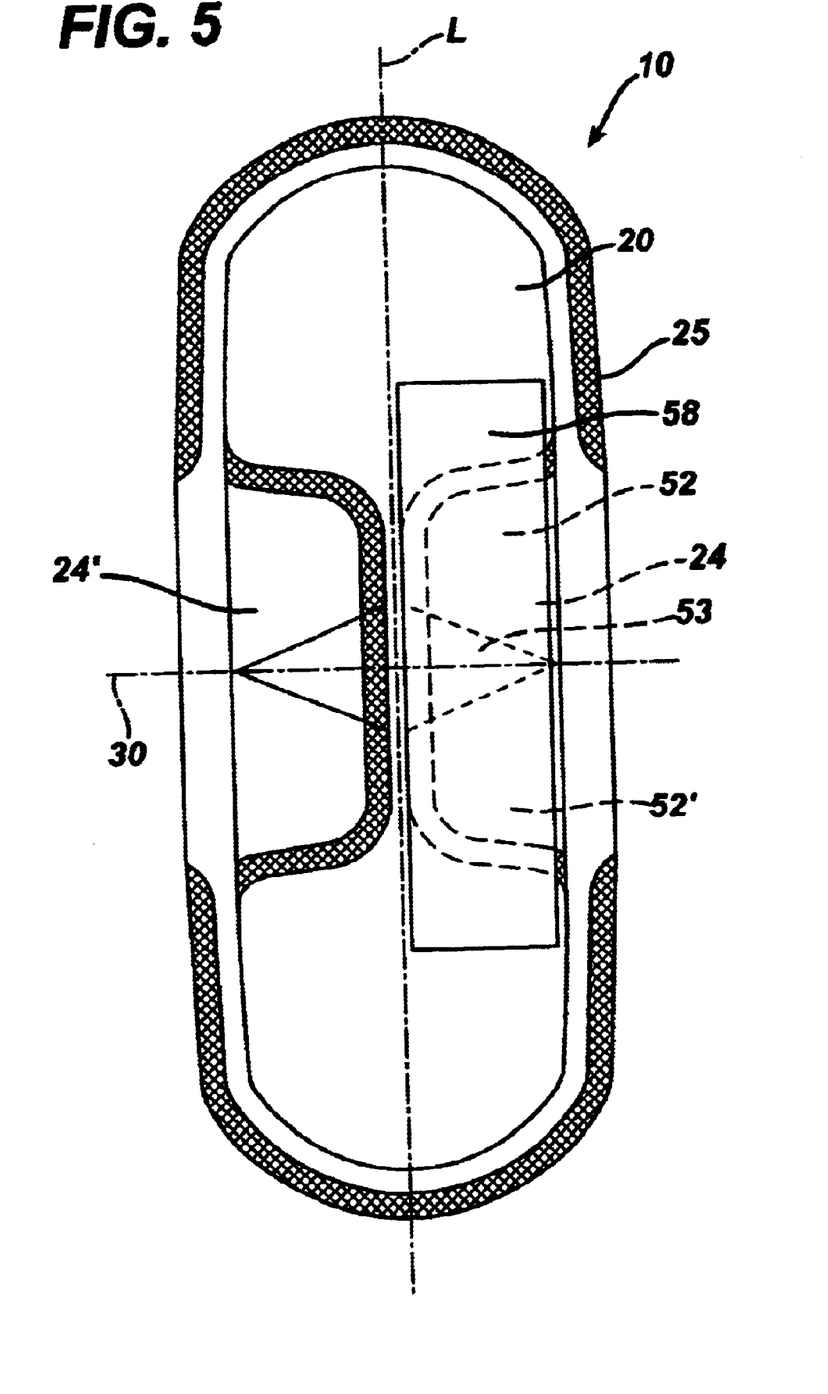
FIG. 5 is a bottom plan view of another embodiment of the present invention.

FIG. 5 shows a sanitary napkin 10 with flaps 24, 24' formed proximal of the longitudinal side edges of the napkin. In the embodiment shown in FIG. 5 the the flaps 24, 24' are attached to the garment facing side of the pad and are joined proximal (or "inboard") from the longitudinal edges 25, 25' toward the longitudinal centerline. The flaps 24 may optionally be affixed inward from the longitudinal side edges of the central absorbent element 20. In a preferred embodiment, the flaps are affixed slightly inward from the longitudinal side edges, generally between 2 mm to 10 mm inward from the side edge. In an alternative embodiment, each flap may be joined to the central absorbent element 20 along the principal longitudinal centerline. Thus, the flap may be joined at any place between the principal longitudinal centerline and the longitudinal edges 25, 25' of the central absorbent element 20. The flaps 24, 24' will, of course, generally be on opposite sides of the principal longitudinal centerline.

Figure 6:
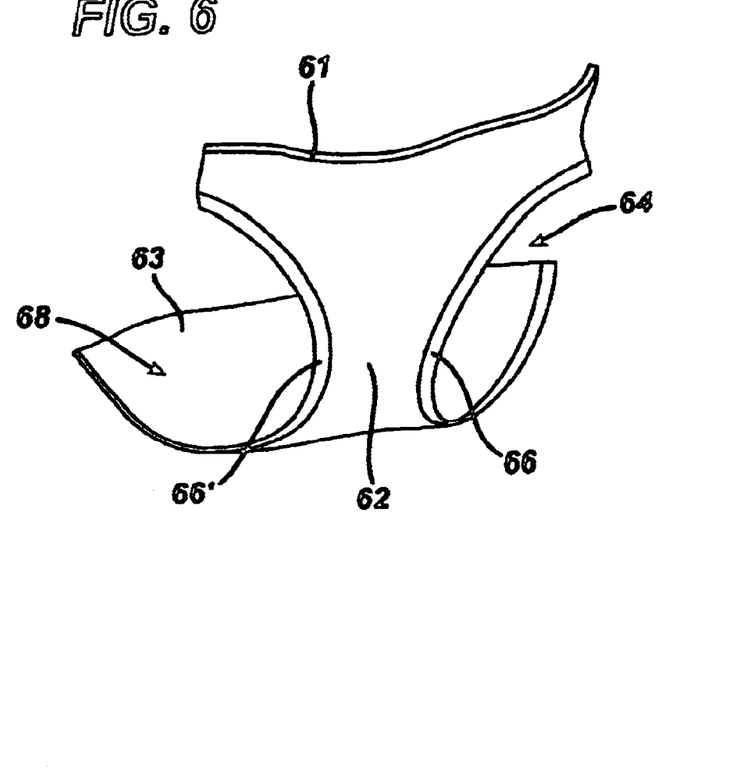
FIG. 6 is a perspective view of the crotch portion of a woman's undergarment.

FIG. 6 is a depiction of a crotch portion 64 of an undergarment 61 of a type that is conventionally worn by many women. The undergarment 61 comprises a front section 62, a back section 63 and a crotch portion 64. The crotch portion comprises two side edges 66, 66'. The undergarment has an inner surface 68.

Figure 7:
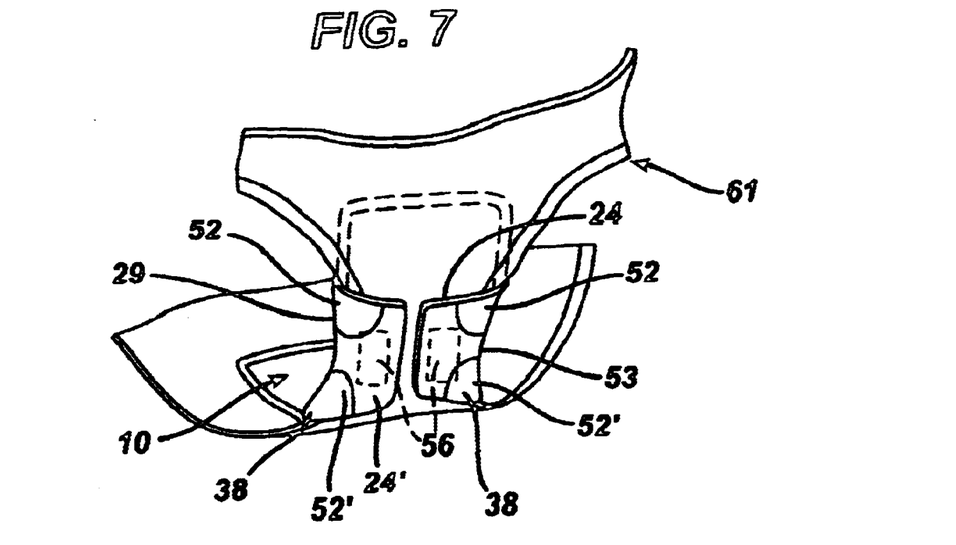
FIG. 7 is the same perspective view of the woman's undergarment shown in FIG. 6 with the sanitary napkin embodiment of FIG. 1 being placed therein for use.

The sanitary napkin 10 of the present invention is utilized by placing the sanitary napkin 10 in a wearer's undergarment 61 as shown in FIG. 7. The center of central absorbent element 20 is placed in the crotch portion 64 of the undergarment with one end of central absorbent element 20 extending towards the front section 62 of the undergarment and the other end towards the back section 62. The backsheet 17 is placed in contact with the inner surface 68 of center crotch portion 64 of the undergarment. Central pad adhesive 54 maintains central absorbent element 20 in position. The freely extending distal portions of the flaps 24, 24' are folded around the side edges 66, 66' of the undergarment along fold line 29. The flap adhesive 56 secures the flap 24 to the underside of the undergarment.

In use, the stresses imparted to the flaps by the undergarment are most highly concentrated along the fold line 29 where the flap 24 changes from being disposed on the body-faceable side of the undergarment to being located on the garment-faceable side of the undergarment. In other words, the stresses are concentrated at the edge 66 of the crotch portion 64 of the undergarment 61. The stresses in the flaps 24 generally follow the arc formed by the edges 66 of the crotch portion 64. Depending on the design of the sanitary napkin, the stresses are generally concentrated in an arc that may or may not coincide with the lines of juncture 26 between the flaps 24 and the central absorbent element 20. These stresses may cause the corner regions 52, 52' of the flaps 24, 24' to bunch longitudinally inward toward the lateral centerline of the flap. This reduces the area of the wearer's undergarments the flaps are able to cover. If the stresses are great enough, the flaps 24 can become detached from the undergarment and the flaps 24 will be less than optimally effective.

In order to eliminate, or at least reduce these stresses, the flaps 24, 24' are adapted to reduce the stresses along the fold line 29 to such a degree that the flaps 24 will remain attached to the underside of the undergarment and will not lose their ability to cover a given area of the wearer's undergarment. The corner regions of the flap are capable of extending longitudinally outward from the flap lateral centerline in an amount sufficient to smoothly cover the edges 66 of the undergarment when the sanitary napkin is worn.

Figure 8:
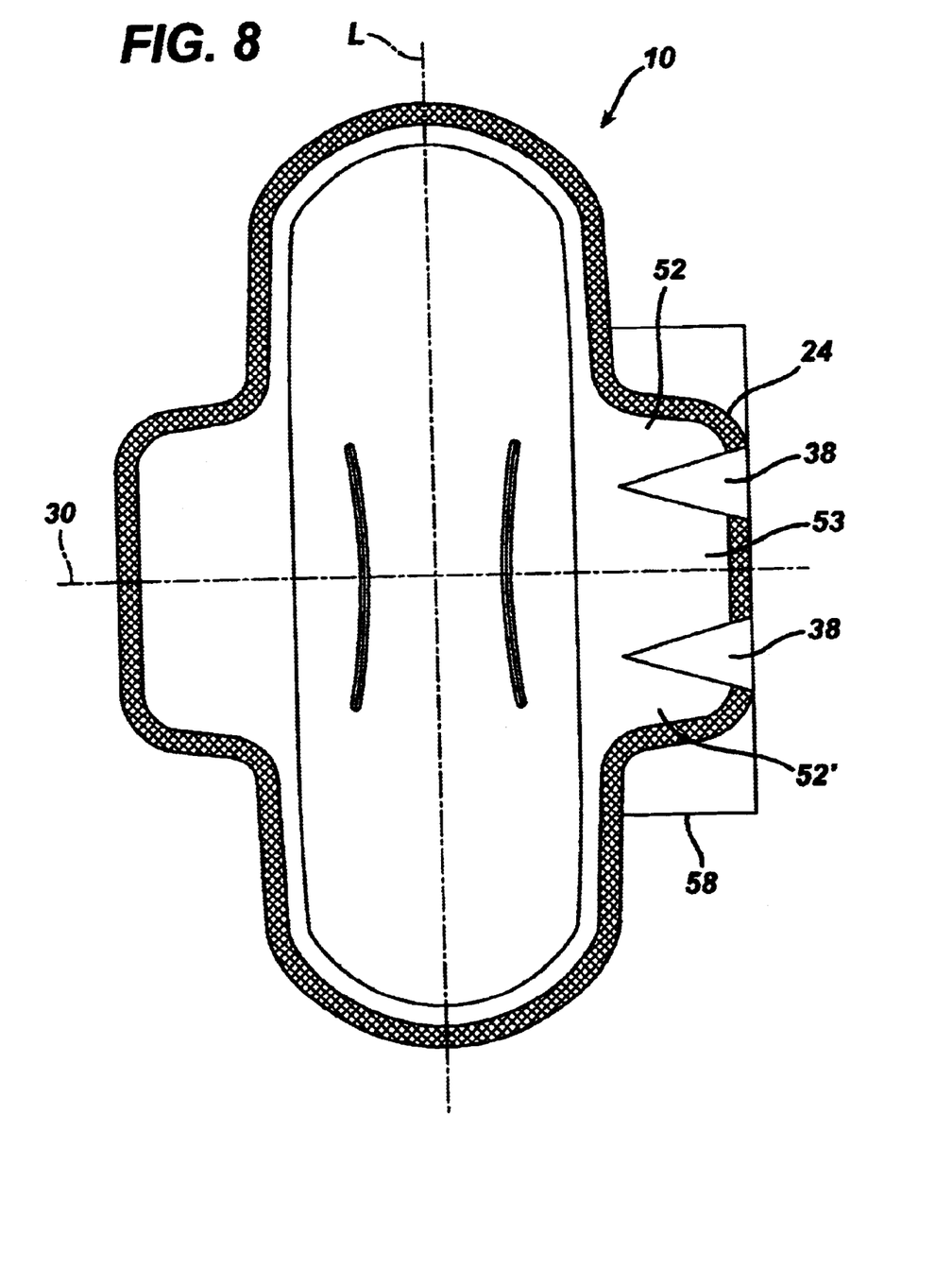
FIG. 8 is a top plan view of an another embodiment of the present invention.

FIG. 8 shows another alternative embodiment to the sanitary napkin 10 of the present invention in which the flaps 24, 24' are attached along longitudinal edges 25, 25'. In this embodiment, the central portion of the flap incorporates two zones formed from an expandable elastic material to provide additional stress relief to the flaps.

Figure 9:
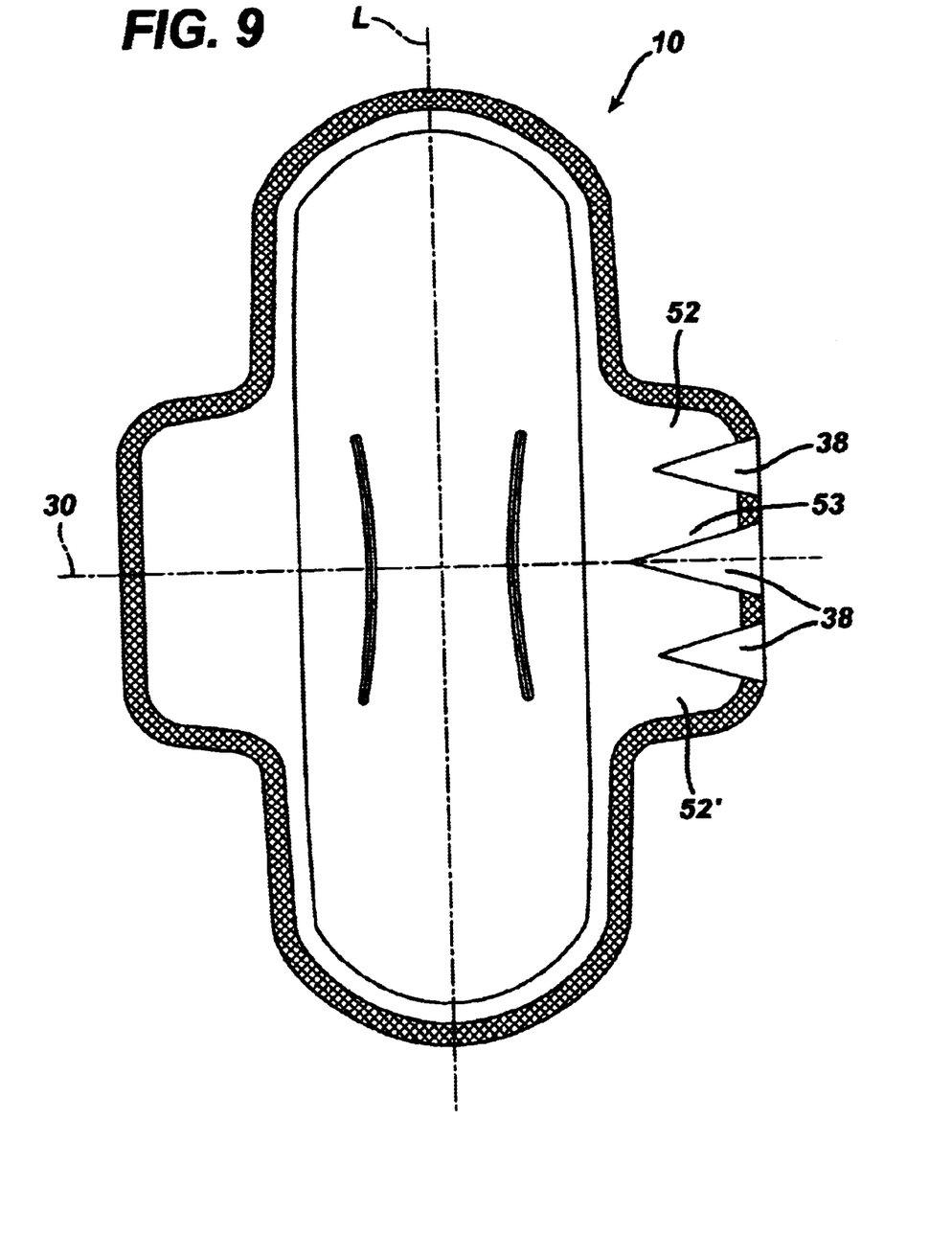
FIG. 9 is a top plan view of an another embodiment of the present invention.

FIG. 9 shows another alternative embodiment to the sanitary napkin 10 of the present invention in which the flaps 24, 24' are attached along longitudinal edges 25, 25'. In this embodiment, the central portion of the flap incorporates three zones formed from an expandable elastic material to provide additional stress relief to the flaps.

While particular embodiments of the present invention have been illustrated and described, it would be obvious to those skilled in the art that various other changes and modifications can be made without departing from the spirit and scope of the invention.

What is claimed:

1. A sanitary napkin comprising a central absorbent element having a cover layer, a barrier layer and an absorbent core between the cover layer and the barrier layer, the central absorbent element having opposite longitudinally extending edges and opposite lateral ends, a flap extending laterally from each respective longitudinally extending edge along a line of juncture and adapted to be folded over a crotch portion of an undergarment in use, each flap having a central region and a corner region adjacent the line of juncture and a lateral centerline extending through the central region and bisecting the flap into first half and a second half;

the central region of the flap along the flap lateral centerline being formed from a flexible, elastic material having an elastic modulus and at least a portion of the corner region being formed from a substantially non-elastic material wherein the central portion is capable of elastically expanding in use and the corner region is capable of smoothly folding over the crotch portion of the undergarment in use wherein the line of juncture is a longitudinally oriented straight line of attachment.

2. A sanitary napkin comprising a central absorbent element having a cover layer, a barrier layer and an absorbent core between the cover layer and the barrier layer, the central absorbent element having opposite longitudinally extending edges and opposite lateral ends, a flap extending laterally from each respective longitudinally extending edge along a line of juncture and adapted to be folded over a crotch portion of an undergarment in use, each flap having a central region and a corner region adjacent the line of juncture and a lateral centerline extending through the central region and bisecting the flap into first half and a second half;

the central region of the flap along the flap lateral centerline being formed from a flexible, elastic material having an elastic modulus and at least a portion of the corner region being formed from a substantially nonelastic material wherein the central portion is capable of elastically expanding in use and the corner region is capable of smoothly folding over the crotch portion of the undergarment in use wherein the line of juncture is a longitudinally oriented plurality of intermittent lines or points of attachment.

3. A sanitary napkin comprising a central absorbent element having a cover layer, a barrier layer and an absorbent core between the cover layer and the barrier layer, the central absorbent element having opposite longitudinally extending edges and opposite lateral ends,     a flap extending laterally from each respective longitudinally extending edge along a line of juncture and adapted to be folded over a crotch portion of an undergarment in use, each flap having a central region and a corner region adjacent the line of juncture and a lateral centerline extending through the central region and bisecting the flap into first half and a second half;

the central region of the flap along the flap lateral centerline being formed from a flexible, elastic material having an elastic modulus and at least a portion of the corner region being formed from a substantially nonelastic material wherein the central portion is capable of elastically expanding in use and the corner region is capable of smoothly folding over the crotch portion of the undergarment in use wherein flaps are affixed to and extend laterally from a line of juncture on a garment faceable side of the sanitary napkin inward from the longitudinally extending edges of the central absorbent element.

\* \* \* \* \*